(12) United States Patent
Sode et al.

(10) Patent No.: US 7,807,351 B2
(45) Date of Patent: Oct. 5, 2010

(54) METHOD OF DETECTING TARGET MOLECULE BY USING APTAMER

(75) Inventors: Koji Sode, Tokyo (JP); Kazunori Ikebukuro, Tokyo (JP)

(73) Assignee: Techno Medica Co., Ltd., Yokohama-Shi (JP)

( * ) Notice: Subject to any disclaimer, the term of this patent is extended or adjusted under 35 U.S.C. 154(b) by 792 days.

(21) Appl. No.: 10/580,044

(22) PCT Filed: Nov. 22, 2004

(86) PCT No.: PCT/JP2004/017665

§ 371 (c)(1), (2), (4) Date: Jan. 19, 2007

(87) PCT Pub. No.: WO2005/049826

PCT Pub. Date: Jun. 2, 2005

(65) Prior Publication Data

US 2008/0254446 A1    Oct. 16, 2008

(30) Foreign Application Priority Data

Nov. 22, 2003    (JP) ............................ 2003-431323

(51) Int. Cl.
*C12Q 1/68* (2006.01)
*C12N 9/74* (2006.01)

(52) U.S. Cl. .......................................... 435/6; 435/214

(58) Field of Classification Search ................ 536/24.3; 435/6, 214

See application file for complete search history.

(56) References Cited

U.S. PATENT DOCUMENTS

| 5,582,981 | A | 12/1996 | Toole et al. | |
|---|---|---|---|---|
| 5,888,739 | A | 3/1999 | Pitner et al. | |
| 6,680,377 | B1 * | 1/2004 | Stanton et al. | 536/22.1 |
| 2005/0089864 | A1 * | 4/2005 | Li et al. | 435/6 |
| 2005/0176940 | A1 * | 8/2005 | King | 536/23.1 |

FOREIGN PATENT DOCUMENTS

| EP | 0 826 780 A1 | 3/1998 |
|---|---|---|
| JP | 6-508022 A | 9/1994 |
| JP | 10-084983 A | 4/1998 |
| WO | WO-92/14843 A1 | 9/1992 |
| WO | WO 00/79004 A1 | 12/2000 |
| WO | WO 01/09158 A1 | 2/2001 |
| WO | WO 01/57259 A1 | 8/2001 |

OTHER PUBLICATIONS

Feigon et al., "Aptamer structures from A to zeta," Chemistry & Biology, vol. 3, No. 8, pp. 611-617, 1996, XP 002340205.
Nutiu et al., "Structure-Switching Signaling Aptamers," Journal of the American Chemical Society, vol. 125, No. 16, pp. 4771-4778, XP 002374937.
Ikebukuro et al., "Novel strategy for DNA aptamers inhibiting enzymatic activity using algorithim mimicking evolution," Nucleic Acids Research Supplement, No. 3, pp. 205-206, 2003, XP 002459706.
Yoshida et al., "Homgeneous DNA sensing using enzyme-inhibiting DNA aptamers," Biochemical and Biophysical Research Communications, vol. 348, No. 1, pp. 245-252, 2006, XP 005593057.
Yoshida et al., "Aptameric Enzyme Subunit for Biosensing Based on Enzymatic Activity Measurement," Analytical Chemistry, vol. 78, No. 10, pp. 3296-3303, 2006, XP 003010513.
N. Hamaguchi et al., 2001, Anal Biochem, 294(2), pp. 126-131.
T. Hermann et al., 2000, Science, 287 (5454), pp. 820-825.
S.E. Osborne et al., 1997, Chem. Rev. 97(2), pp. 349-370.
L. JJ et al., 2002, Biochem. Biophys. Res. Commun., 292(1), pp. 31-40.
Tuerk et al., Science, vol. 249, pp. 505-510. Aug. 3, 1990.

* cited by examiner

*Primary Examiner*—Gary Benzion
*Assistant Examiner*—Cynthia B Wilder
(74) *Attorney, Agent, or Firm*—Birch, Stewart, Kolasch & Birch, LLP (57) ABSTRACT

An aptamer-probe complex for detecting the presence of a target molecule is disclosed. The complex of the present invention contains an aptamer moiety which is able to bind to an indicator protein and change the properties of the indicator protein, and a probe moiety which is able to bind to a target molecule, wherein the aptamer moiety and the probe moiety are combined in such a manner that the binding mode between the aptamer moiety and the indicator protein changes when the probe moiety binds to the target molecule. A target molecule can be detected with combination of an aptamer which binds to a certain protein, and a probe which binds to the target molecule, utilizing the properties of that protein as an indicator.

7 Claims, 10 Drawing Sheets

METHOD OF DETECTING TARGET MOLECULE BY USING APTAMER

TECHNICAL FIELD

The present invention relates to a method for detecting a target molecule with a combination of an aptamer that binds to a certain protein and a probe that binds to the target molecule utilizing the properties of that protein as an indicator.

BACKGROUND ART

In a typical method for detecting a target nucleotide sequence, a probe DNA having a nucleotide sequence complementary to that sequence is synthesized, and hybridization of the probe DNA with a target nucleic acid is detected. The hybridization process typically consists of preparing a probe coupled to a fluorescent substance or radioactive isotope, such as a probe labeled with a fluorescent substance or radioactive isotope, hybridizing the probe with DNA that contains a target nucleotide sequence, and detecting a signal emitted by the label by measuring the fluorescent intensity or radioactivity. In addition, in a method for detecting a target protein or a small molecule, a substance capable of binding to the target, such as an antibody, ligand or receptor, is labeled with a fluorescent substance or radioactive isotope, and then measuring the fluorescent intensity, radioactivity or enzyme activity.

Although improvement of those methods has made it possible to detect a target molecule at concentrations on the nanomolar level, there is a growing demand in the art for detection methods with even higher sensitivity. In addition, since a spectrophotometer or fluorescent microscope is required for measuring fluorescence, and a scintillation counter is required for measuring radioactivity, detection of target molecules by conventional methods requires expensive and large equipments. Furthermore, since the majority of conventional methods require separation of label that has been bound to the target and label that has not bound to the target (bound/free (B/F) separation), which makes the procedure complicated. Consequently, there is a need for the development of a simple detection method that does not require special analytical instruments or B/F separation.

Thus, an object of the present invention is to provide a novel method for detecting a target molecule with a simple process and a high sensitivity.

DISCLOSURE OF THE INVENTION

The inventors found that a target can be detected with a complex comprising a combination of an aptamer which binds to a certain protein and changes the properties of the protein, and a probe capable of binding to a target, wherein the changes in the properties of the protein is utilized as an indicator.

The present invention provides an aptamer-probe complex for detecting the presence of a target molecule. The aptamer-probe complex of the present invention comprises an aptamer moiety which is able to bind to an indicator protein and change the properties of the indicator protein, and a probe moiety which is able to bind to the target molecule, wherein the aptamer moiety and the probe moiety are combined in such a manner that the binding mode between the aptamer moiety and the indicator protein changes when the probe moiety binds to the target molecule.

In one preferable embodiment of the aptamer-probe complex of the present invention, the target molecule is a nucleic acid, and the probe moiety of the aptamer-probe complex is an oligonucleotide capable of hybridizing with the nucleic acid. In another preferable embodiment, the target molecule is a protein or a small molecule, and the probe moiety of the aptamer-probe complex is an aptamer capable of binding to the protein or the small molecule.

The indicator protein is preferably an enzyme, and particularly preferably thrombin.

In another preferable embodiment of the present invention, binding between the aptamer moiety and the indicator protein becomes stronger when the probe moiety binds to the target molecule. In another preferable embodiment, binding between the aptamer moiety and the indicator protein becomes weaker when the probe moiety binds to the target molecule.

Preferable examples of a target molecule to be detected by the aptamer-probe complex of the present invention include *Salmonella* bacteria and SARS virus genes or a portion thereof.

In another aspect, the present invention provides a kit for detecting the presence of a target protein comprising the aptamer-probe complex of the present invention.

In still another aspect, the present invention provides a method for detecting the presence of a target molecule in a sample with the aptamer-probe complex of the present invention, comprising contacting a sample to be tested for the presence or amount of a target molecule with the aptamer-probe complex of the present invention, and detecting the change in the properties of the indicator protein as an indication of the presence of the target molecule. In the case that the indicator protein is an enzyme, the change in enzyme activity can be measured by spectrophotometric techniques or electrochemical techniques.

PREFERRED EMBODIMENT OF THE INVENTION

Structure of Aptamer-Probe Complex

An aptamer-probe complex of the present invention is a polynucleotide composed of an aptamer moiety and a probe moiety. The polynucleotide may be DNA or RNA, or a nucleic acid mimic such as PNA. The polynucleotide may also contain various modifications in the bases, sugars and/or internucleotide linkages.

An "aptamer moiety" refers to a region that acts as an aptamer on an indicator protein, and is able to bind to the indicator protein and change the properties of the protein. As used herein, an "aptamer" represents a nucleic acid ligand that binds to a specific molecule. The concept of aptamers was first reported by Gold et al. in 1990. Aptamers can be obtained by a method referred to as Systematic Evolution of Ligands by Exponential enrichment (SELEX) (Tuerk, C. and Gold L. (1990), Systematic evolution of ligands by exponential enrichment: RNA ligands to bacteriophage T4 DNA polymerase. Science, 249, 505-510). Examples of targets for which aptamers have been obtained include: T4 DNA polymerase, R17 coat protein, MS2 coat protein, E. coli S1 protein, E. coli rho protein, E. coli 30S particle+S1, E. coli 30S particle-S1, E. coli metJ protein, QB replicase, HIV-1 Rev protein, HIV-1 tat protein, HIV-1 int protein, HIV-1 reverse transcriptase, MMLV reverse transcriptase, AMV reverse transcriptase, FIV reverse transcriptase, HTLV-1 rex peptide, U1A, U2AF, thrombin, elastase, sPLA2, NGF, bFGF, VEGF, anti-gp-10 antibody, SLE monoclonal antibody, anti-insulin receptor, IgE, human chorionic gonadotropin, thrombin, theophylline, FMN, AMP, arginine, citrulline, tobramycin, neomycin B, hematoporphyrin, chitin and cholic acid (Hermann, et al., (2000), Adaptive recognition by nucleic acid aptamers, Science 287, 820-825). A more detailed explanation relating to the selection and application of aptamers can be found in Osborne S E, Ellington A D. (1997), Nucleic Acid Selection and the Challenge of Combinatorial Chemistry. Chem. Rev. April 1; 97(2): 349-370.

A "probe moiety" is a region that is able to bind to a target molecule to be detected. In the case that the target molecule is a nucleic acid, the probe moiety is an oligonucleotide capable of hybridizing with the nucleic acid. For example, a complex of the present invention can be designed so that a probe moiety is attached to the 3' side of an aptamer moiety and binding between the aptamer moiety and indicator protein is inhibited when the probe moiety is hybridized with a target molecule. Alternatively, a complex of the present invention may be designed so that the probe moiety inhibits binding between the aptamer moiety and the indicator protein in the absence of a target molecule. In this case, when the probe moiety is hybridized with the target molecule, such an inhibitory action of the probe moiety is diminished, resulting in enhanced binding between the aptamer moiety and indicator protein. In addition, a complex of the present invention can be designed so that a nucleotide sequence of the probe moiety is inserted into the nucleotide sequence of the aptamer moiety, and binding between the aptamer moiety and an indicator protein is inhibited when the probe moiety is hybridized with a target molecule. In another embodiment, a complex of the present invention may also be designed to have probe moieties on both 5' and 3' sides of the aptamer moiety, where a part of the nucleotide sequence complementary to the target sequence is attached to the 5' side, and another part of the complementary sequence is attached to the 3' side of the aptamer moiety.

In the case that the target molecule is a protein or a small molecule, an aptamer capable of binding to the protein or the small molecule can be used as the probe moiety. In this context, the aptamer does not represent the aptamer moiety of an aptamer-probe complex of the present invention which binds to an indicator protein, but rather serves as a probe moiety which binds to a target molecule. Namely, in this embodiment of the present invention, a complex of the present invention has two aptamer sequences directed to different targets.

The aptamer moiety and the probe moiety are coupled by a covalent bond. Preferably, the aptamer moiety and the probe moiety form a single linear or circular polynucleotide. An aptamer-probe complex of the present invention can be easily prepared by solid-phase synthesis on a DNA synthesizer.

An "indicator protein" refers to a protein that produces a detectable signal as a result of a change in its properties. Examples of the indicator protein include enzymes, fluorescent proteins, receptors, and ligands that bind to specific receptors. A preferable indicator protein is an enzyme. Thrombin is particularly suitable for use as an indicator protein in the present invention, since the thrombin activity may be readily measured and a plurality of aptamers have been reported that inhibit the thrombin activity. Aptamers that bind to virtually any types of enzymes could be obtained by SELEX. Such an aptamer may be sequenced and used for designing an aptamer-prove complex according to the present invention in combination with that enzyme as an indicator protein.

The aptamer-probe complex of the present invention is characterized in that the binding mode between the aptamer moiety and the probe moiety will change when the probe moiety binds to a target molecule, resulting in the change of the properties of the indicator protein. This change in the binding mode is believed to be due to a change in the structure of the aptamer moiety of the aptamer-probe complex, or due to steric inhibition attributable to the structure of the probe moiety. However, the present invention is not limited by the predicted mechanism of the change in the binding mode.

In a preferable embodiment of the present invention, binding between the aptamer moiety and the indicator protein becomes stronger as a result of the probe moiety binding to a target molecule. In the case that the indicator protein is an enzyme, inhibition of enzyme activity by the aptamer moiety will increase when binding between the aptamer moiety and the enzyme becomes stronger, resulting in a decrease in enzyme activity. In another preferable embodiment, binding between the aptamer moiety and an indicator protein becomes weaker as a result of the probe moiety binding to a target molecule. In the case that the indicator protein is an enzyme, inhibition of enzyme activity by the aptamer moiety is diminished when binding between the aptamer moiety and enzyme becomes weaker, resulting in increased enzyme activity. Namely, in either of those embodiments, the presence of a target molecule can be easily detected by measuring the activity of the indicator protein, i.e., an enzyme.

One example of a target molecule to be detected by the aptamer-probe complex of the present invention is a nucleic acid. In this case, the probe moiety of the aptamer-probe complex is an oligonucleotide capable of hybridizing with that nucleic acid. Any nucleic acid may be used as the target nucleic acid. Examples of the nucleic acid to be detected include bacteria or virus genes, such as Salmonella bacteria or SARS virus genes, or a portion thereof, DNA and RNA present in cells or tissues, and synthesized or isolated DNA and RNA. In addition, an aptamer-probe complex of the present invention is also useful for detecting single nucleotide mutations in the genome.

Another example of a target molecule to be detected by the aptamer-probe complex of the present invention is a protein or a small molecule. In this case, an aptamer capable of binding to the protein or the small molecule is used as the probe moiety of the aptamer-probe complex. Any proteins or small molecules may be used as the target protein or small molecule. Specific aptamers have already been identified for various proteins and small molecules, and aptamers that bind to virtually any molecules could be obtained by SELEX. Thus, any types of protein or small molecule may be used as a target molecule according to the present invention as far as an aptamer specific to the target molecule could be obtained.

Method for Detecting Target Molecule

In another aspect, the present invention provides a method for detecting the presence of a target molecule in a sample with the aptamer-probe complex of the present invention. The method comprises contacting a sample to be tested for the presence of a target molecule with an aptamer-probe complex of the present invention, detecting the change in the properties of the indicator protein as an indication of the presence of the target molecule in the sample.

In the case that the indicator protein is an enzyme, the target molecule can be easily detected by measuring the change in the properties of the indicator protein as a change in the enzyme activity. A change in enzyme activity can be determined by measuring the enzyme activity with spectrophotometric techniques or electrochemical techniques. For example, thrombin activity is measured by using N-benzyl-Phe-Val-Arg-p-nitroanilide as a substrate and measuring the level of released p-nitroaniline at the optical density of 410 nm. Thrombin activity can also be measured by adding fibrinogen and thrombin to a constant final concentration in plasma, and measuring blood coagulation which is triggered by cleavage of fibrinogen by thrombin. Various methods are available for measuring blood coagulation, for example, measurement of the change in refractive index using a spectrophotometric method, adding metal spheres to plasma and observing when their movement stops as the blood coagulates, crystal vibrator, surface plasmon resonance, and interference enhanced reflection (IER). In addition, any enzymes that are conventionally used as a detection label can be used in the invention, such as luciferase, chloramphenicol acetyl transferase, alkaline phosphatase and horseradish peroxidase.

Various methods can be used for detecting the enzyme reaction, such as conventionally used colorimetry. Preferred is an electrochemical method, which enables simplified measurement system, reduced size, integrated system and commercial production.

In the case of using a receptor as the indicator protein, a substance that is released from binding or dissociation between the receptor and a ligand corresponding to the receptor can be detected by spectrophotometry. In addition, in the case of using a fluorescent protein as the indicator protein, the fluorescent properties of the fluorescent protein are monitored.

According to the present invention, a target molecule is mixed with an aptamer-probe complex of the present invention, and binding between a target molecule and the probe moiety can be observed directly without separating unbound components, which is required in conventional methods. Thus, a target molecule can be detected easily with a high sensitivity.

Kit for Detecting Target Molecule

In another aspect, the present invention provides a kit for detecting the presence of a target molecule comprising the aptamer-probe complex of the present invention. In addition to the aptamer-probe complex of the present invention, the kit may also comprise an indicator protein, various reagents and solutions for measuring the properties of the indicator protein, and instructions for use. The aptamer-probe complex of the present invention can be provided in various forms, such as a freeze-dried reagent or a solution in a suitable storage medium.

Sensor for Detecting Target Molecule

The aptamer-probe complex of the present invention is suitable for use as a recognition element of a sensor for detecting a target molecule. In the sensor for detecting a target molecule, the aptamer-probe complex of the present invention can be attached to an electrode or semiconductor chip for measuring a change in the properties of an indicator protein. Examples of electrodes include a carbon electrode, gold electrode or platinum electrode. The aptamer-probe complex of the present invention may be immobilized on the electrode. The aptamer-probe complex of the present invention may be immobilized on an electrode by avidin-biotin binding, a crosslinking reagent, encapsulating the aptamer-probe complex into a polymer matrix, coating the aptamer-probe complex with a dialysis membrane, or by entrapping the aptamer-probe complex in a photocrosslinking polymer, electrically conductive polymer or oxidation-reduction polymer. In the entrapping methods, the aptamer-probe complex may optionally be immobilized in a polymer together with an electron mediator, such as ferrocene or a derivative thereof, or adsorbed onto an electrode. For example, in the case of using an enzyme as the indicator protein, the aptamer-probe complex is immobilized on a carbon electrode by means of avidin-biotin binding, enzyme is added to the measurement system, and then the sample is added and the enzyme reaction product is electrochemically measured to detect the presence of a target molecule in the sample.

In one example, the detection of a target molecule can be carried out in the manner described below. A buffer solution is placed in a constant-temperature cell and maintained at a constant temperature. An electrode (such as a carbon electrode) immobilized with an aptamer-probe complex is used as an working electrode, and a counter electrode (such as a platinum electrode) and reference electrode (such as an Ag/AgCl electrode) are provided. After adding a test sample and contacting it with the aptamer-probe complex, an indicator protein (i.e. an enzyme) is added. After incubating for a predetermined amount of time, a constant voltage is applied to the electrodes and a substrate is added. The increase in current caused by the interaction between the enzyme reaction product and the electrode is measured. The concentration of the target molecule in the sample can then be calculated from a calibration curve prepared from standard solutions containing predetermined concentrations of the target molecule.

Examples of Structure of Aptamer-Probe Complex

Various aspects of the present invention will be described with reference to the drawings. The structures of the aptamer-probe complex shown in the drawings are merely intended to serve as schematic representations for explaining the principle and concept of the present invention, and are not intended to limit the three-dimensional structure of the complex of the present invention, the binding mode with an indicator protein, or the way of changes in the binding mode.

Figure 1:
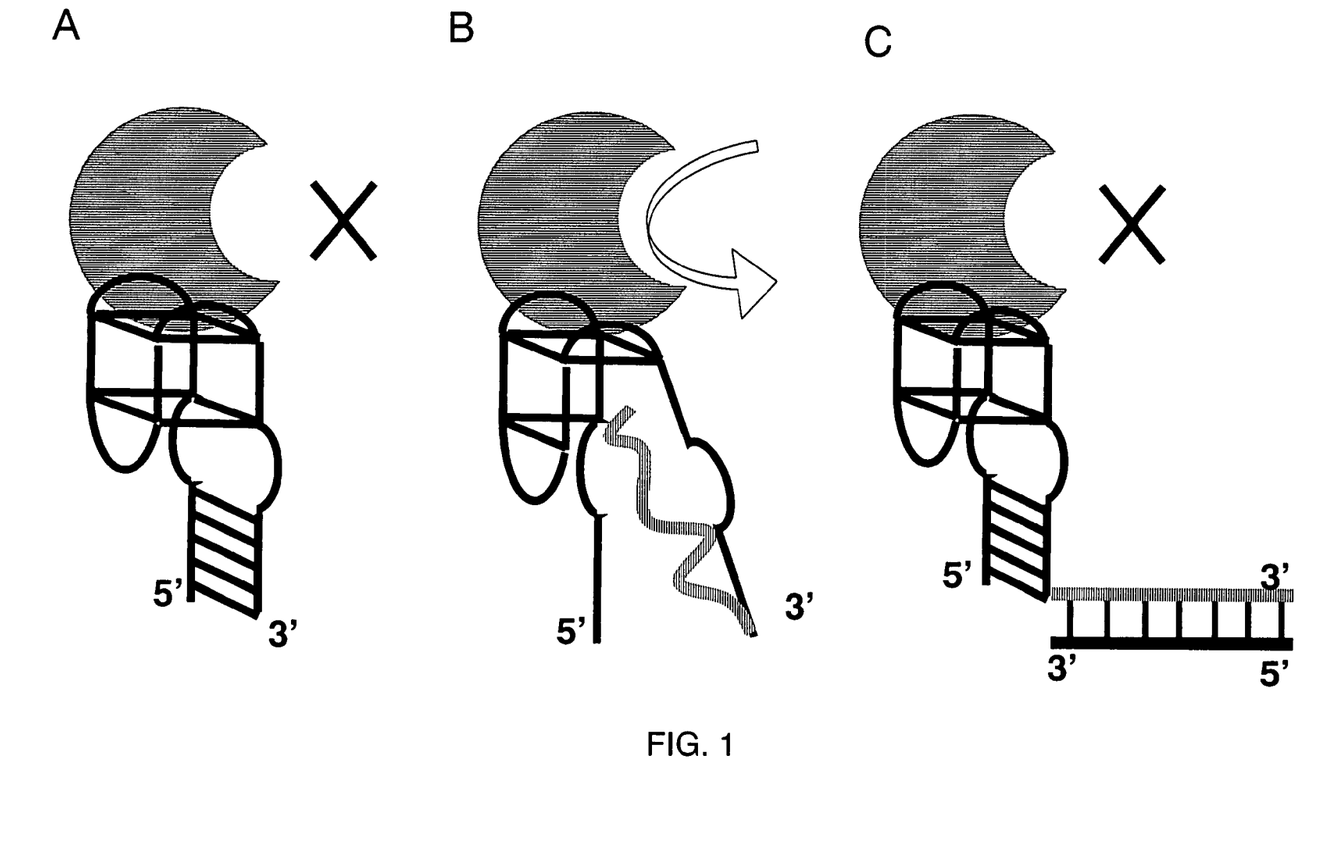
FIG. 1 shows an example of an aptamer-probe complex in which binding between the aptamer moiety and an indicator protein becomes stronger when hybridization occurs between the probe moiety and a target DNA.

FIG. 1 shows an example of an aptamer-probe complex in which binding with an indicator protein becomes stronger when hybridization occurs between the probe moiety and a target DNA. This type of aptamer-probe complex may be DNA comprising a thrombin aptamer sequence as the aptamer moiety, and a sequence complementary to a portion of *Salmonella* invA gene as the probe moiety on the 3' side of the aptamer moiety (FIG. 1A). The indicator protein is thrombin, and the aptamer moiety is capable of binding to thrombin to inhibit its enzyme activity. The target molecule is *Salmonella* invA gene. Where *Salmonella* invA gene is not present, the aptamer moiety is unable to strongly bind to thrombin due to the presence of the probe sequence, and thrombin exhibits its activity (FIG. 1B). If *Salmonella* invA gene is present, the probe moiety hybridizes with the *Salmonella* invA gene to form a stable double-strand DNA structure, and the aptamer moiety binds to thrombin strongly, thus the enzyme activity of thrombin is inhibited (FIG. 1C). Example 1 shows the method and results of an experiment in which thrombin activity was measured with the aptamer-probe complex of FIG. 1 in the presence or absence of a target molecule.

Figure 4:
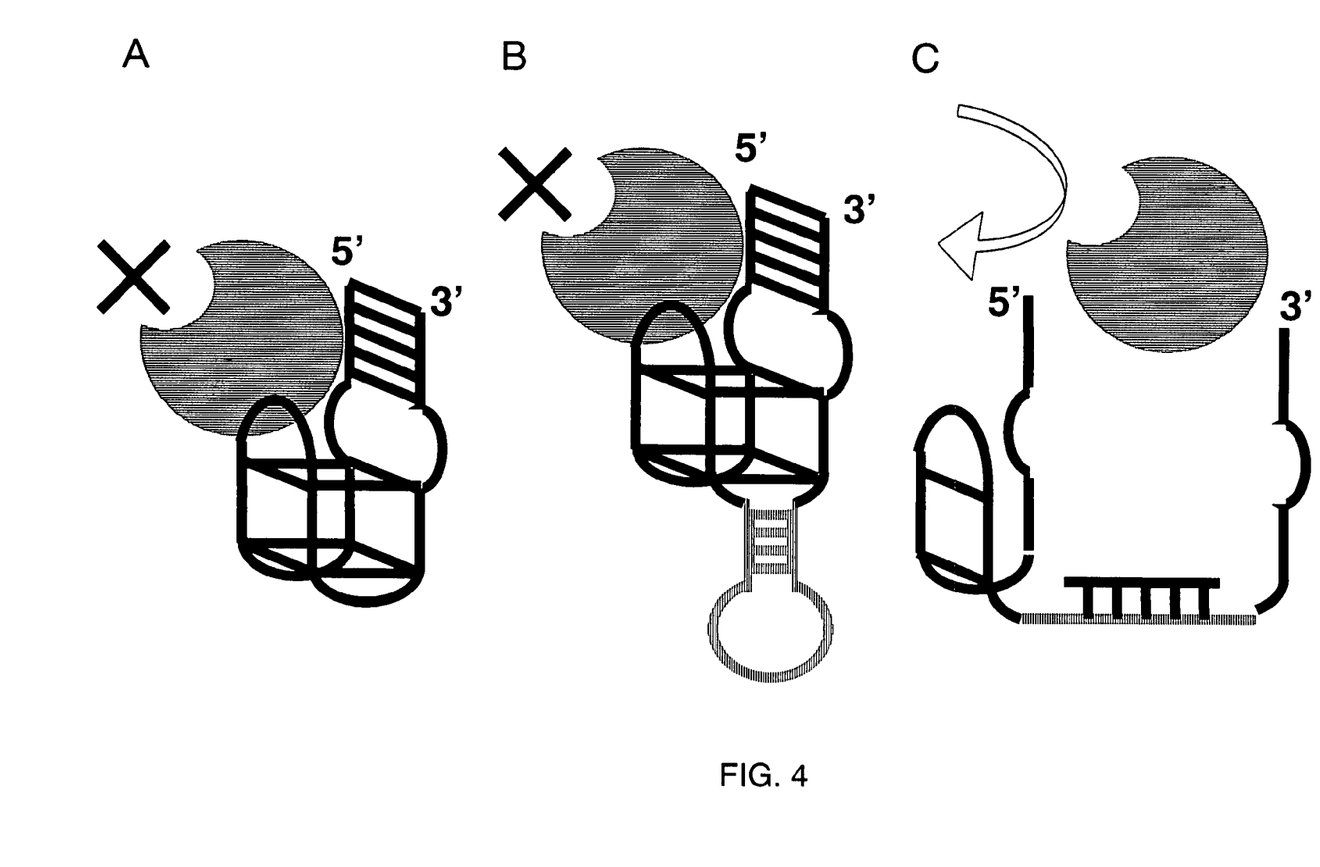
FIG. 4 shows an example of an aptamer-probe complex in which binding between the aptamer moiety and an indicator protein becomes weaker when hybridization occurs between the probe moiety and a target DNA.

FIG. 4 shows an example of an aptamer-probe complex in which binding with an indicator protein becomes weaker when hybridization occurs between the probe moiety and a target DNA. This type of aptamer-probe complex has a thrombin aptamer sequence as the aptamer moiety, and a stem-loop structure is inserted into the aptamer moiety and serves as the probe moiety which contains the sequence complementary to a portion of SARS virus gene (FIG. 4B). The target molecule is SARS virus gene. Where SARS virus gene is not present, the probe moiety forms a stable stem-loop structure and the aptamer moiety binds to thrombin to inhibit its enzyme activity. If SARS virus gene is present, the probe moiety hybridizes with the SARS virus gene and the stem-loop structure is destroyed, which affects binding between the aptamer moiety and thrombin. Thus, the aptamer moiety is unable to bind strongly to thrombin, and thrombin exhibits its enzyme activity (FIG. 4C). Example 2 shows the method and results of an experiment in which the activity of thrombin was measured with the aptamer-probe complex of FIG. 4 in the presence or absence of a target molecule.

Figure 7:
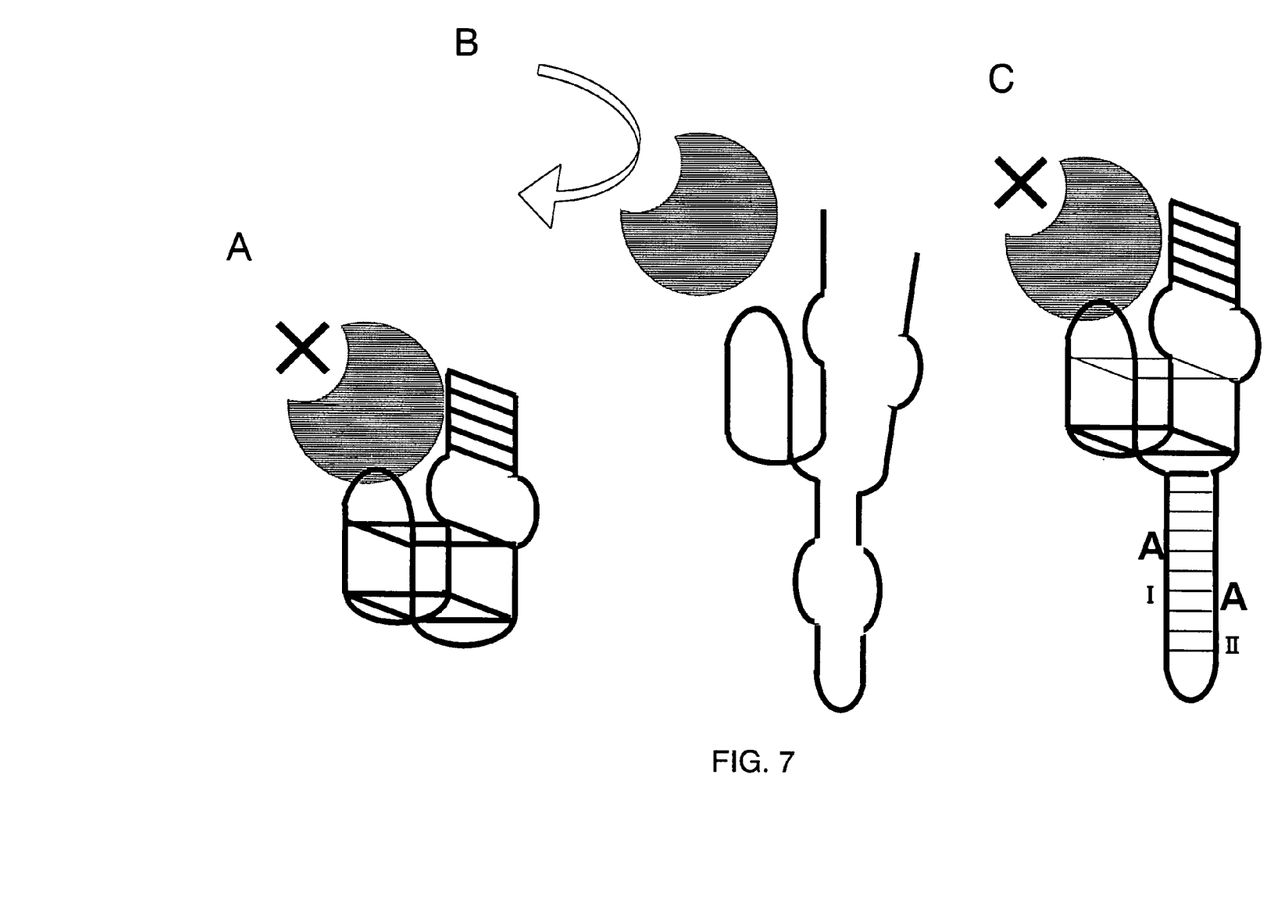
FIG. 7 shows an aptamer-probe complex in which binding between the aptamer moiety and an indicator protein becomes stronger when the probe moiety binds to a target molecule.

FIG. 7 shows an example of an aptamer-probe complex in which binding with an indicator protein becomes stronger when the probe moiety binds to a target small molecule. This type of aptamer-probe complex has a thrombin aptamer sequence as the aptamer moiety, and an ATP aptamer sequence capable of binding to adenosine is inserted into the thrombin aptamer sequence as the probe moiety (FIG. 7B). It should be noted here that the ATP aptamer does not act as an aptamer moiety that binds to an indicator protein, but rather acts to bind to a target molecule as the probe moiety of the aptamer-probe complex of the present invention. The target molecule is adenosine. Where adenosine is not present, the aptamer moiety is unable to strongly bind to thrombin due to the presence of the sequence of the probe moiety, and thrombin exhibits its enzyme activity (FIG. 7B). If adenosine is present, the ATP aptamer sequence of the probe moiety binds to the adenosine to form a stable complex. Consequently, binding between the aptamer moiety and thrombin becomes stronger and the enzyme activity of thrombin is inhibited (FIG. 7C). Example 3 shows the method and results of an experiment in which the activity of thrombin was measured with the aptamer-probe complex of FIG. 7 in the presence or absence of a target molecule.

The contents of all patents and references expressly cited in the specification are incorporated herein by reference in its entirety. In addition, the contents described in the specification and drawings of Japanese Patent Application No. 2003-431323, which serves as the basis for the claiming of priority of the present application, are incorporated herein by reference in its entirety.

EXAMPLES

Hereinafter, the present invention will be described in more detail with reference to Examples of detecting *Salmonella* invasion factor-related invA gene (invA gene), SARS virus gene and adenosine, however, the present invention is not limited to these Examples.

Example 1

A thrombin-invA aptamer was synthesized based on a known thrombin aptamer sequence. *Salmonella* invA gene was used as the target DNA. A schematic representation of the structure of this type of aptamer-probe complex is shown in FIG. 1.

```
Thrombin aptamer:
                                              (SEQ ID NO. 1)
5'CACTGGTAGGTTGGTGTGGTTGGGGCCAGTG3'

Thrombin-invA aptamer:
                                              (SEQ ID NO. 2)
5'CACTGGTAGGTTGGTGTGGTTGGGGCCAGTGGGCATCAATACTCATC-
TGTTTACCGGG3'

27 mer invA:
                                              (SEQ ID NO. 3)
5'CCCGGTAAACAGATGAGTATTGATGCC3'

27 mer control DNA:
                                              (SEQ ID NO. 4)
5'GAATCCGGTACTGGCTAAGACAACTGT3'
```

Thrombin-invA aptamer at a final concentration of 1 μM was heated at 95° C. for 3 minutes in 50 mM Tris-HCl (final concentration) and 5 mM KCl (pH=8.0) in the presence and absence of the 27 mer invA or 27 mer control DNA at a final concentration of 1 μM, followed by cooling slowly over the course of 30 minutes from 95° C. to room temperature. Subsequently, a fibrinogen solution at a final concentration of 1 mg/ml (Wako Pure Chemical Industries), as well as a mixed solution containing thrombin (Wako Pure Chemical Industries) at a final concentration of 54 nM and thrombin-invA aptamer were incubated at 37° C. for 5 minutes. Five minutes later, the thrombin solution and the fibrinogen solution were mixed and the amount of time required for coagulation was measured using an automated blood coagulation measurement system (KC4A Micro, Amelung). The final concentration of the buffer was 50 mM Tris-HCl, 5 mM KCl and 75 mM NaCl (pH=8.0).

Figure 2:
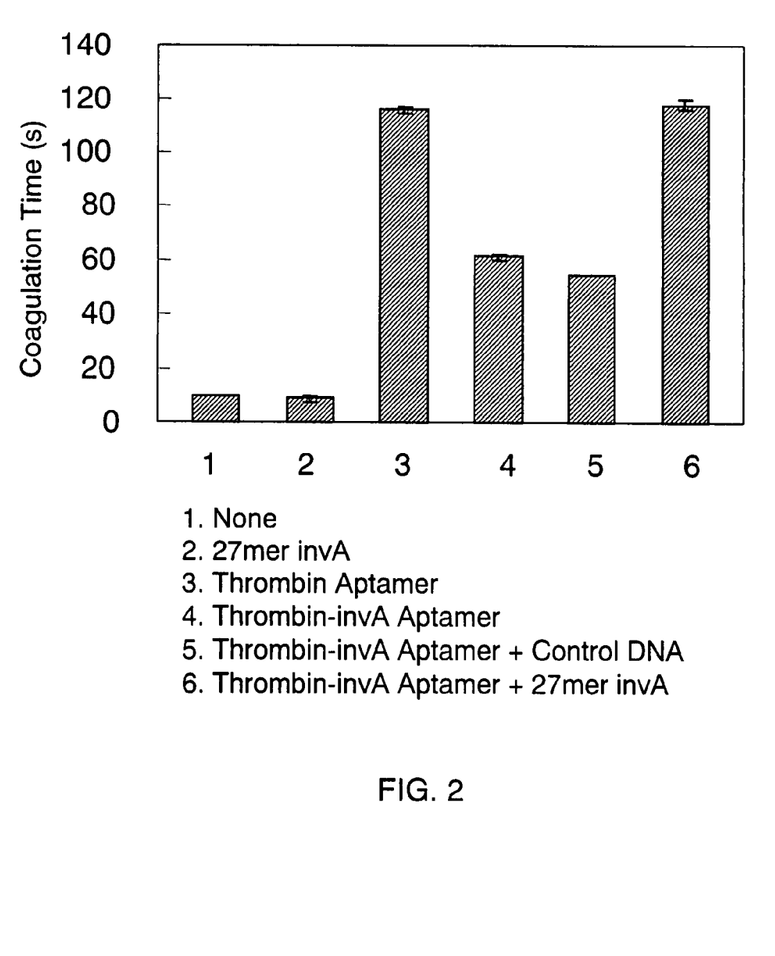
FIG. 2 shows a method for detecting target DNA using the aptamer-probe complex of FIG. 1.

The results are shown in FIG. 2. Coagulation time of the sample containing thrombin-invA aptamer was shorter than that of thrombin aptamer, suggesting that the ability of the aptamer to inhibit thrombin activity decreased when a complementary nucleotide sequence of the 27 mer invA sequence was attached to the 3' end of the thrombin aptamer solution. When the control DNA was added to the thrombin-invA aptamer, coagulation time was almost the same, while the coagulation time increased when the 27 mer invA sequence was added, indicating that the ability of the aptamer to inhibit thrombin is restored in the presence of the 27 mer invA sequence.

Next, the target DNA was quantitatively measured with the thrombin-invA aptamer. Thrombin-invA aptamer at a final concentration of 1 μM was heated at 95° C. for 3 minutes in 50 mM Tris-HCl (final concentration) and 5 mM KCl (pH=8.0) in the presence and absence of 27 mer invA or 27 mer control DNA at a final concentration of 0.1 to 5 μM, and then slowly cooled over the course of 30 minutes from 95° C. to room temperature. Subsequently, a fibrinogen solution at a final concentration of 1 mg/ml (Wako Pure Chemical Industries), as well as a mixed solution containing thrombin at a final concentration of 54 nM (Wako Pure Chemical Industries) and thrombin-invA aptamer were incubated at 37° C. for 5 minutes. Then the thrombin solution and the fibrinogen solution were mixed and the amount of time required for coagulation was measured using an automated blood coagulation measurement system (KC4A Micro, Amelung). The final concentration of the buffer was 50 mM Tris-HCl, 5 mM KCl and 75 mM NaCl (pH=8.0).

Figure 3:
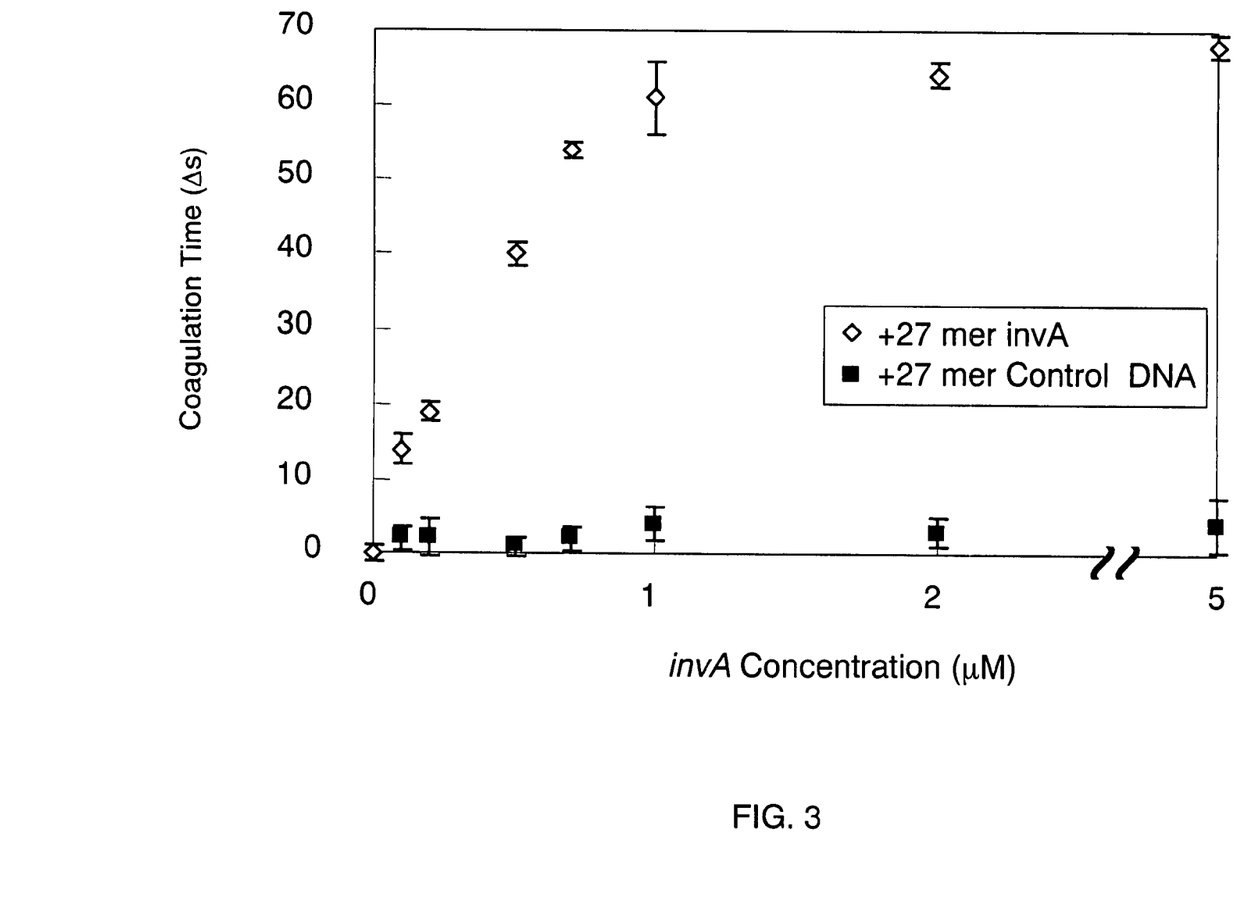
FIG. 3 shows the results of detecting target DNA using the aptamer-probe complex of FIG. 1.

The results are shown in FIG. 3. The coagulation time did not change when the control DNA was added to the thrombin-invA aptamer solution. In contrast, when the target DNA was added, the coagulation time increased dependently on the concentration of the target DNA up to a final concentration of 1 μM, and became saturated over that concentration. Namely, it was shown that the target DNA can be detected at 100 nM or more by measuring the enzyme activity of thrombin using a thrombin-invA aptamer at a final concentration of 1 μM.

Example 2

Figure 5:
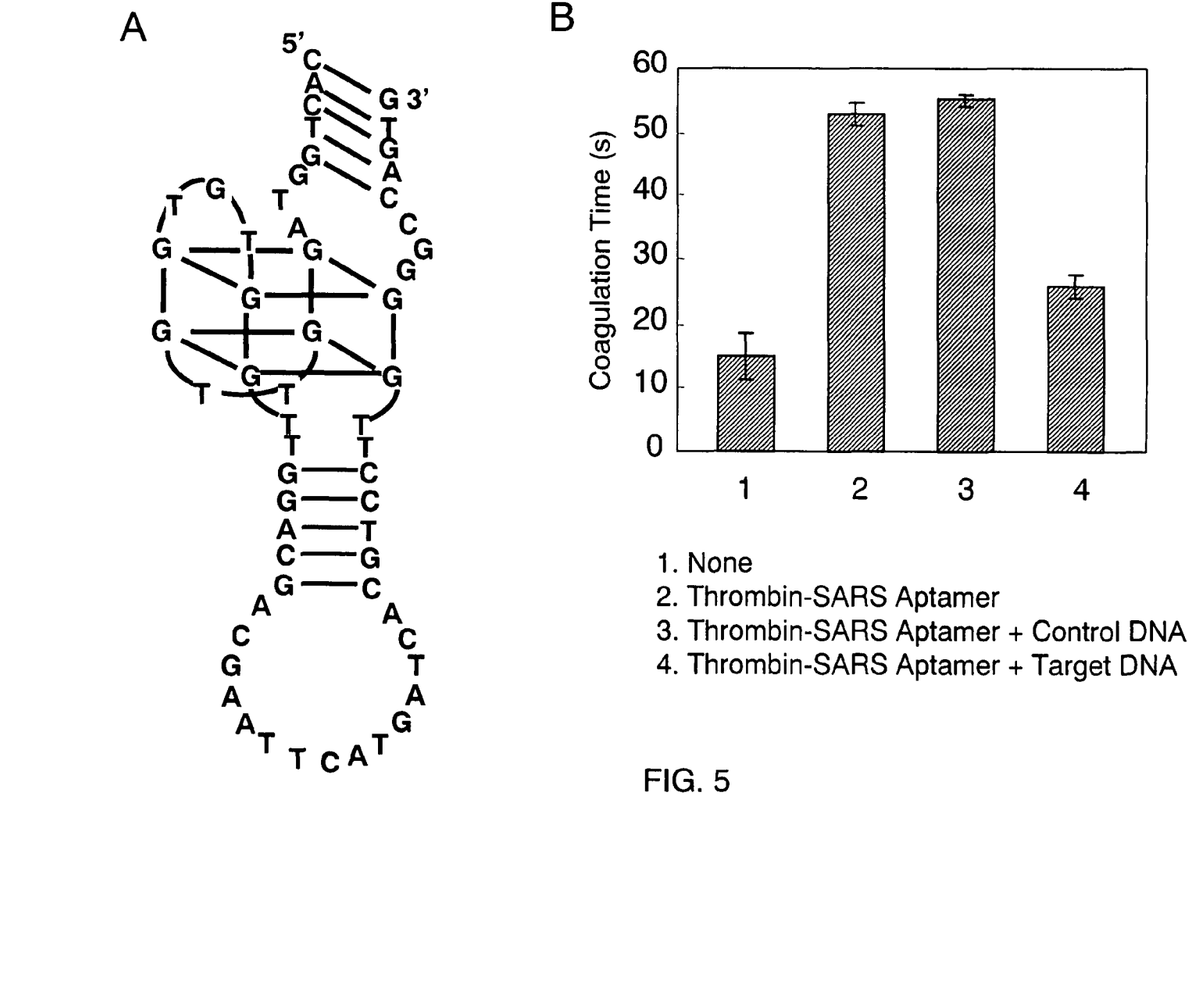
FIG. 5 (SEQ ID NO: 5) shows a method for detecting target DNA using the aptamer-probe complex of FIG. 4.

A thrombin-SARS aptamer was synthesized having the sequence shown below. SARS virus gene was used as the target DNA. A schematic representation of the structure of this type of aptamer-probe complex is shown in FIG. 4 and FIG. 5A (SEQ ID NO: 5).

```
Thrombin aptamer:
                                          (SEQ ID NO. 1)
5'CACTGGTAGGTTGGTGTGGTTGGGGCCAGTG3'

Thrombin-SARS aptamer:
                                          (SEQ ID NO. 5)
5'CACTGGTAGGTTGGTGTGGTTGGACGACGAATTCATGATCACGTCCTT
GGGGCCAGTG3'

15 mer target DNA:
                                          (SEQ ID NO. 6)
5'TGATCATGAATTCGT3'

15 mer control DNA:
                                          (SEQ ID NO. 7)
5'ATTGCTATCGTACAT3'
```

Thrombin-SARS aptamer at a final concentration of 1 μM was heated at 95° C. for 3 minutes in 50 mM Tris-HCl (final concentration) and 5 mM KCl (pH=8.0) in the presence and absence of the 15 mer target DNA or 15 mer control DNA at a final concentration of 1 μM, followed by cooling slowly over the course of 30 minutes from 95° C. to room temperature. Subsequently, a fibrinogen solution at a final concentration of 1 mg/ml, as well as a mixed solution containing thrombin at a concentration of 54 nM (Wako Pure Chemical Industries) and thrombin-SARS aptamer were incubated at 37° C. for 5 minutes. The thrombin solution and the fibrinogen solution were mixed and the amount of time required for coagulation was measured using an automated blood coagulation measurement system (KC4A Micro, Amelung). The final concentration of the buffer was 50 mM Tris-HCl, 5 mM KCl and 75 mM NaCl (pH=8.0).

The results are shown in FIG. 5B. The coagulation time did not change when the 15 mer control DNA was added to the thrombin-SARS aptamer solution. In contrast, when the 15 mer target DNA was added, the coagulation time became shorter, suggesting that the ability of the thrombin-SARS aptamer to inhibit thrombin decreases in the presence of the target DNA.

Next, the target DNA was quantitatively measured with the thrombin-SARS aptamer. Thrombin-SARS aptamer at a final concentration of 1 μM was heated at 95° C. for 3 minutes in 50 mM Tris-HCl (final concentration) and 5 mM KCl (pH=8.0) in the presence and absence of 15 mer target DNA or 15 mer control DNA at a final concentration of 0.1 to 5 μM, and then slowly cooled over the course of 30 minutes from 95° C. to room temperature. Subsequently, a fibrinogen solution at a final concentration of 1 mg/ml (Wako Pure Chemical Industries), as well as a mixed solution containing thrombin at a concentration of 54 nM (Wako Pure Chemical Industries) and thrombin-SARS aptamer were incubated at 37° C. for 5 minutes. Five minutes later, the thrombin solution and the fibrinogen solution were mixed and the amount of time required for coagulation was measured using an automated blood coagulation measurement system (KC4A Micro, Amelung). The final concentration of the buffer was 50 mM Tris-HCl, 5 mM KCl and 75 mM NaCl (pH=8.0).

Figure 6:
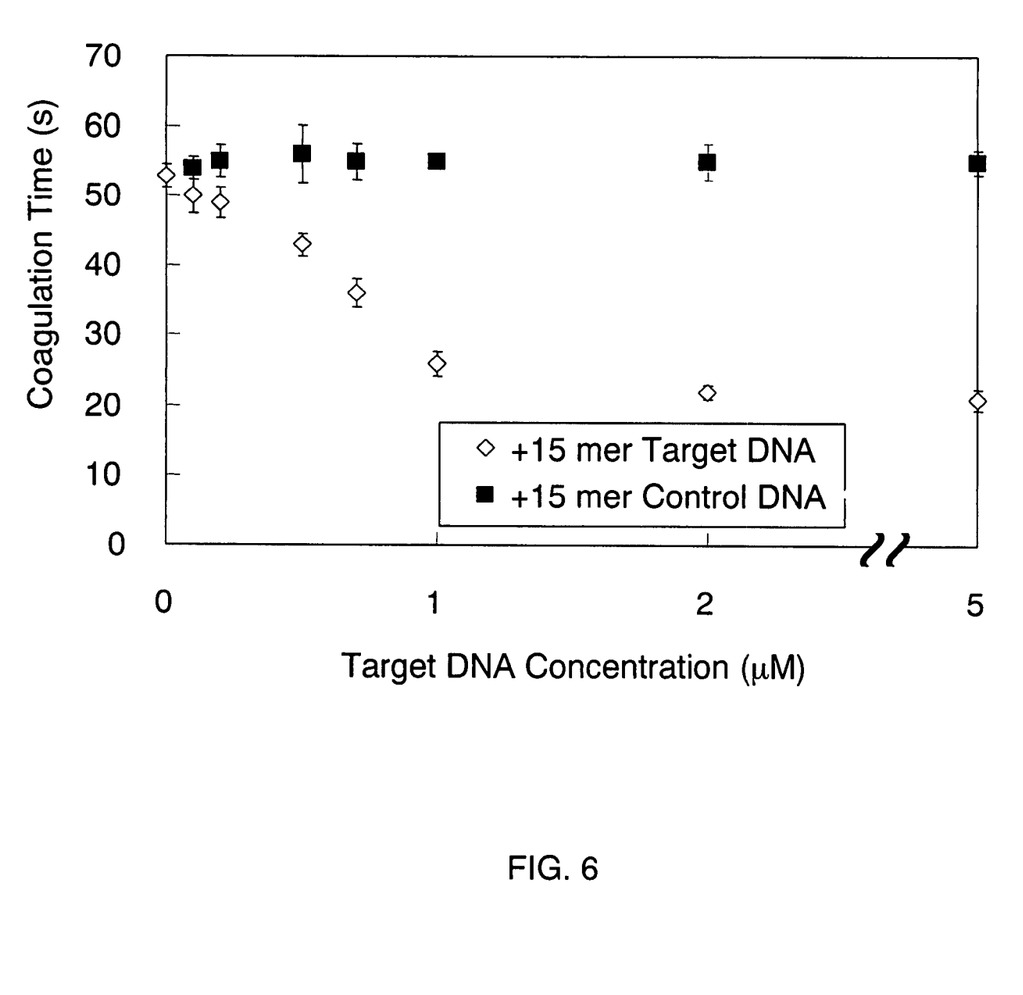
FIG. 6 shows the results of detecting target DNA using the aptamer-probe complex of FIG. 4.

The results are shown in FIG. 6. The coagulation time did not change when the 15 mer control DNA was added to the thrombin-SARS aptamer. In contrast, when the target DNA was added, the coagulation time decreased dependently on the concentration of the target DNA up to a final concentration of 1 μM, and became saturated over that concentration. Namely, it was shown that the target DNA can be detected at 200 nM or more by measuring the enzyme activity of thrombin using a thrombin-SARS aptamer at a final concentration of 1 μM.

Example 3

A thrombin-ATP aptamer was synthesized having the sequence shown below. Adenosine was used as the target molecule. A schematic representation of the structure of this type of aptamer-probe complex is shown in FIG. 7.

```
Thrombin aptamer:
                                          (SEQ ID NO. 1)
5'CACTGGTAGGTTGGTGTGGTTGGGGCCAGTG3'

Thrombin-ATP aptamer:
                                          (SEQ ID NO. 8)
5'CACTGGTAGGTTGGTGTGGTTCTGGGGGAGTATTGCGGAGGAAGTTGG
GGCCAGTG3'
```

Thrombin-ATP aptamer at a final concentration of 1 μM was heated at 95° C. for 3 minutes in 50 mM Tris-HCl (final concentration) and 5 mM KCl (pH=8.0), followed by cooling slowly over the course of 30 minutes from 95° C. to room temperature. Subsequently, a fibrinogen solution at a final concentration of 1 mg/ml (Wako Pure Chemical Industries), as well as a mixed solution containing thrombin at a concentration of 54 nM (Wako Pure Chemical Industries), thrombin-ATP aptamer and adenosine at a final concentration of 1 mM (Wako Pure Chemical Industries) were incubated at 37° C. for 5 minutes. Five minutes later, the thrombin solution and the fibrinogen solution were mixed and the amount of time required for coagulation was measured using an automated blood coagulation measurement system (KC4A Micro, Amelung). The final concentration of the buffer was 50 mM Tris-HCl, 5 mM KCl and 75 mM NaCl (pH=8.0).

Figure 8:
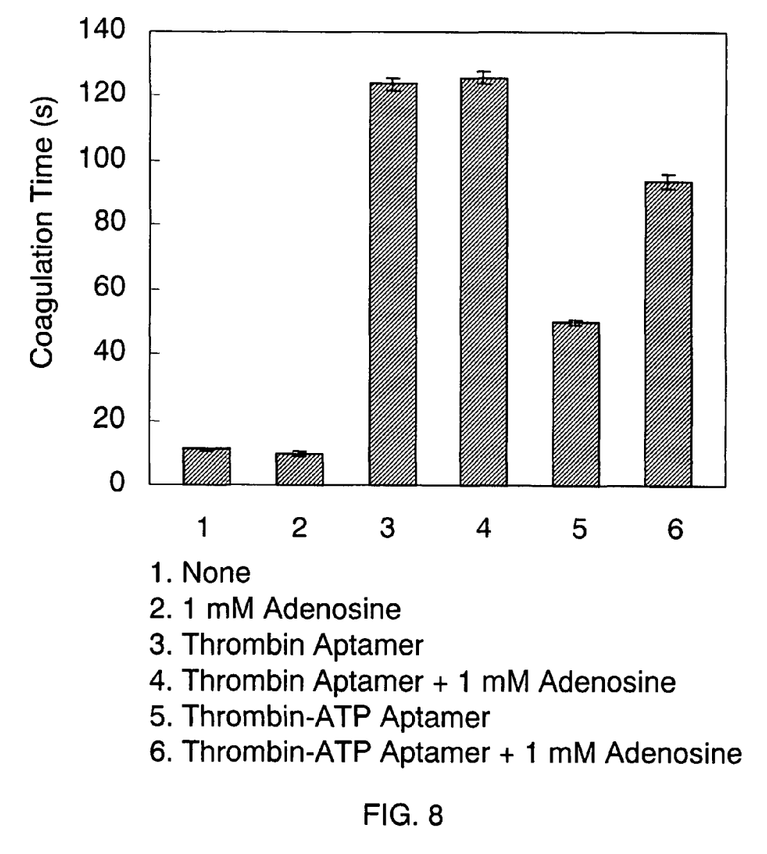
FIG. 8 shows a method for detecting a target molecule using the aptamer-probe complex of FIG. 7.

The results are shown in FIG. 8. The coagulation did not change when adenosine was added at a final concentration of 1 mM to the thrombin or thrombin-ATP aptamer solution. In contrast, when adenosine was added at a final concentration of 1 mM to the thrombin-ATP aptamer, coagulation time increased, suggesting that the ability of the thrombin-ATP aptamer to inhibit thrombin is inhibited in the presence of adenosine.

Next, the adenosine was quantitatively measured with the thrombin-ATP aptamer. Thrombin-ATP aptamer at a final concentration of 1 μM was heated at 95° C. for 3 minutes in 50 mM Tris-HCl (final concentration), 5 mM KCl and 5 mM MgCl$_2$ (pH=8.0), and then slowly cooled over the course of 30 minutes from 95° C. to room temperature. Subsequently, a fibrinogen solution at a final concentration of 1 mg/ml (Wako Pure Chemical Industries), as well as a mixed solution containing thrombin at a final concentration of 54 nM (Wako Pure Chemical Industries), thrombin ATP-aptamer and adenosine or cytidine at a final concentration of 0.01 to 5 mM (Wako Pure Chemical Industries) were incubated at 37° C. for 5 minutes. The thrombin solution and the fibrinogen solution were mixed and the amount of time required for coagulation was measured using an automated blood coagulation measurement system (KC4A Micro, Amelung). The final concentration of the buffer was 50 mM Tris-HCl, 5 mM KCl, 75 mM NaCl and 5 mM MgCl$_2$ (pH=8.0).

Figure 9:
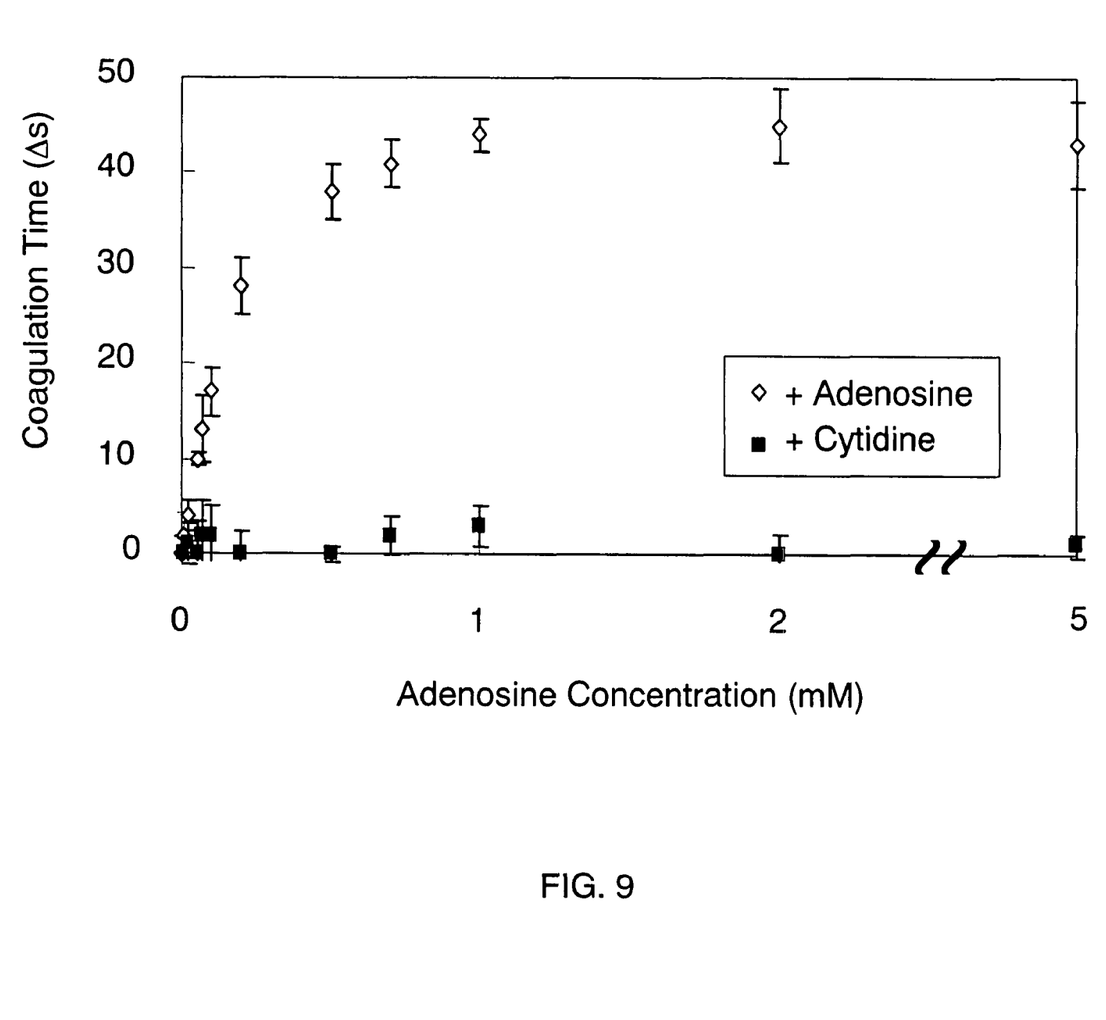
FIG. 9 shows the results of detecting a target molecule using the aptamer-probe complex of FIG. 7; and, FIG. 10 shows the results of detecting target DNA using another embodiment of the aptamer-probe complex of the invention.

The results are shown in FIG. 9. The coagulation time did not change when cytidine was added to the thrombin-ATP aptamer solution. In contrast, when adenosine was added, the coagulation time increased dependently on the concentration of the adenosine up to a final concentration of 1 μM, and became saturated over that concentration. Namely, it was shown that adenosine can be detected at 50 μM or more by measuring the enzyme activity of thrombin using a thrombin-ATP aptamer at a final concentration of 1 μM.

Example 4

A thrombin-invA-3'5' aptamer was synthesized having a nucleotide sequence complementary to an 18 mer portion of *Salmonella* invA gene on both 5' and 3' ends of a thrombin aptamer. The probe sequence was designed so that the Tm values of the sequences added to both ends were the same (Tm value=58°). The sequences of the thrombin-invA-3'5' aptamer, 36 mer DNA having a target nucleotide sequence (invADNA) and 36 mer DNA used as the control (control DNA) are shown below.

Thrombin aptamer:
(SEQ ID NO. 1)
CACTGGTAGGTTGGTGTGGTTGGGGCCAGTG

Thrombin-invA-3'5' aptamer:
(SEQ ID NO. 9)
ACTCATCTGTTTACCGGGCACTGGTAGGTTGGTGTGGTTGGGGCCAGTGC

TTCAAATCGGCATCAAT

InvADNA:
(SEQ ID NO. 10)
CCCGGTAAACAGATGAGTATTGATGCCGATTTGAAG

Control DNA:
(SEQ ID NO. 11)
ATTGTACTTGGACTGTGCATTAGCATGTTACAGTCA

Thrombin was dissolved in a buffer of 50 mM Tris-HCl and 100 mM NaCl (pH=8.0), and diluted to a suitable concentration for use in this assay. N-benzyl-Phe-Val-Arg-p-nitroanilide at a final concentration of 200 μM was used as a thrombin substrate, and thrombin activity was determined by measuring the level of the released p-nitroanilide at the optical density of 410 nm. A solution of 36 mer DNA having invA sequence at a concentration of 0.1 to 1 μM was added to thrombin-invA-3'5' aptamer at a final concentration of 1 μM. The mixture was incubated at 95° C. for 3 minutes, cooled from 95° C. to room temperature over 30 minutes, and the inhibition of thrombin by the aptamer was measured in the presence of invADNA. As a control, the 36 mer control DNA was added instead of the invADNA, and thrombin activity was measured in the same manner. In addition, complementary strands of 0.1 and 1 μM invADNA were added to a solution containing thrombin-invA-3'5' aptamer at a final concentration of 1 μM and invADNA at a final concentration of 1 μM, heat treated in the same manner and measured the enzyme activity of thrombin.

Figure 10:
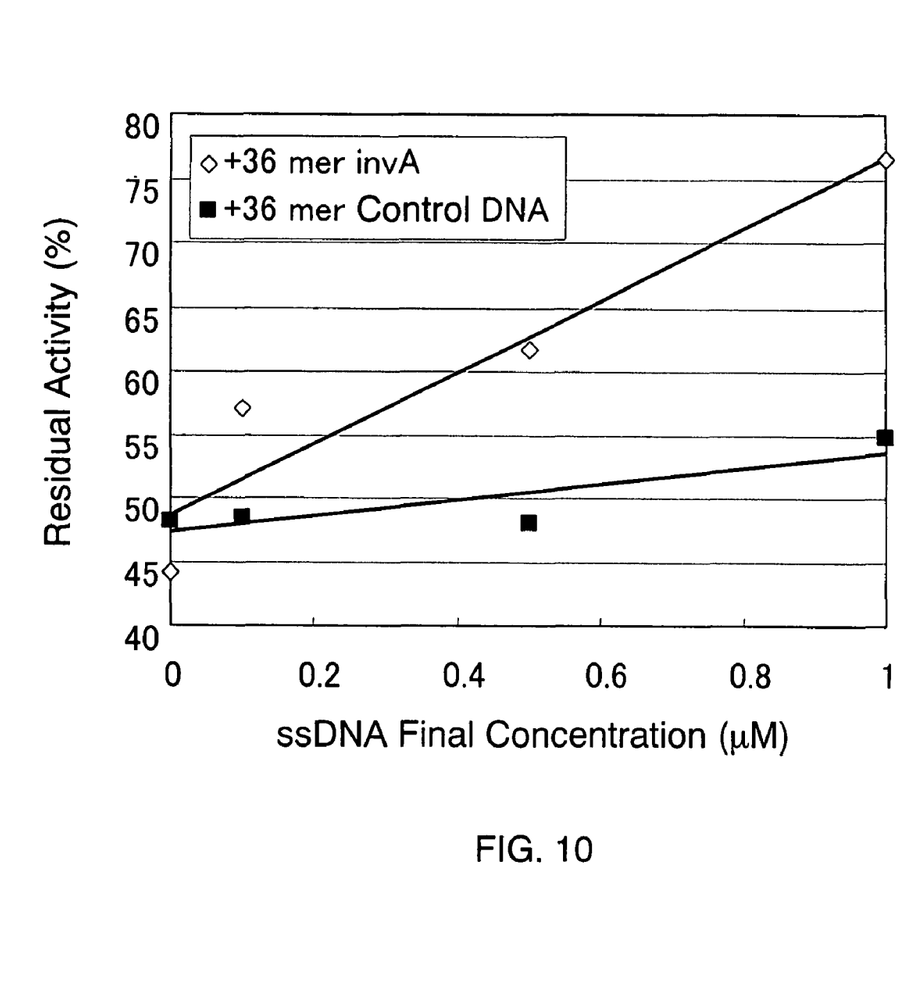

The results are shown in FIG. 10. Inhibition of the enzyme activity of thrombin by thrombin-invA-3'5' aptamer was diminished when the invA sequence was added at a concentration of 0.1 μM or more. In addition, the effect of diminishing inhibition of thrombin enzyme activity decreased when a complementary strand of the invA sequence was added. These results suggested that inhibition of thrombin enzyme activity by thrombin-invA-3'5' aptamer was diminished due to annealing of the invA sequence with the probe sequence.

A solution of 1, 0.5 and 0.1 volumes of 36 mer invADNA was mixed with the thrombin-invA-3'5' aptamer and heat-treated in the same manner as previously described. The products were electrophoresed on 11% polyacrylamide gel to determine the type of the complex formed. The result of the electrophoresis showed that the band attributable to the thrombin-invA-3'5' aptamer became thinner and a plurality of bands were observed as the amount of 36 mer invADNA added to the thrombin-invA-3'5' aptamer increased. These results suggests that the thrombin-invA-3'5' aptamer hybridizes with the 36 mer invADNA and forms several types of complex.

INDUSTRIAL APPLICABILITY

A nucleic acid, protein, small molecule or other target molecule can be detected easily and with high sensitivity by the aptamer-probe complex of the present invention utilizing the properties of a certain protein as an indicator.

The invention claimed is:

1. An aptamer-probe complex for detecting the presence of a target molecule, said complex comprising:
   an aptamer moiety which is able to bind to thrombin and inhibit the enzyme activity of thrombin; and
   a probe moiety which is able to bind to the target molecule, wherein the target molecule is a nucleic acid, and the probe moiety of the aptamer-probe complex is an oligonucleotide capable of hybridizing with the nucleic acid and is located on the 3' side of the aptamer moiety, and wherein when the probe moiety does not bind to the target molecule, said aptamer moiety does not bind to thrombin and thrombin exhibits its activity, and when the probe moiety binds to the target molecule, said aptamer moiety binds to the thrombin and inhibits the enzyme activity of thrombin.

2. An aptamer-probe complex for detecting the presence of a target molecule, said complex comprising:
   a thrombin aptamer moiety which is able to bind to thrombin and inhibit the enzyme activity of thrombin; and
   a probe moiety which is able to bind to the target molecule, wherein the target molecule is a protein or a small molecule, and the probe moiety of the aptamer-probe complex is an aptamer capable of binding to the protein or the small molecule, and is inserted into the sequence of the thrombin aptamer moiety, and wherein when the probe moiety does not bind to the target molecule, said aptamer moiety does not bind to thrombin and thrombin exhibits its activity, and when the probe moiety binds to the target molecule, said aptamer moiety binds to thrombin and inhibits the enzyme activity of thrombin.

3. The complex according to claim 2, wherein the indicator protein is an enzyme.

4. The complex according to claim 3, wherein the enzyme is thrombin.

5. The complex according to claim 1 or 2, wherein the target molecule is Salmonella bacteria gene, SARS virus gene or a portion thereof.

6. A kit for detecting the presence of a target protein, comprising the aptamer-probe complex according to any of claims 1 to 4.

7. An aptamer-probe complex for detecting the presence of a target molecule, said complex comprising:
   an aptamer moiety which is able to bind to thrombin and inhibit the enzyme activity of thrombin; and
   wherein the target molecule is a nucleic acid, and the probe moiety of the aptamer-probe complex is an oligonucleotide capable of hybridizing with the nucleic acid and is inserted into the aptamer moiety with forming a stem-loop structure, and
   wherein when the probe moiety does not bind to the target molecule, said aptamer moiety binds to the thrombin and inhibits the enzyme activity of thrombin, and when the probe moiety binds to the target molecule, said aptamer moiety does not bind to thrombin and thrombin exhibits its activity.

* * * * *

SEQUENCE LISTING

<160> NUMBER OF SEQ ID NOS: 11

<210> SEQ ID NO 1
<211> LENGTH: 31
<212> TYPE: DNA
<213> ORGANISM: Artificial Sequence

```
<220> FEATURE:
<223> OTHER INFORMATION: experimental model for verifying assay system:
      Synthetic Thrombin aptamer

<400> SEQUENCE: 1
cactggtagg ttggtgtggt tggggccagt g                              31

<210> SEQ ID NO 2
<211> LENGTH: 58
<212> TYPE: DNA
<213> ORGANISM: Artificial Sequence
<220> FEATURE:
<223> OTHER INFORMATION: experimental model for verifying assay system:
      Synthetic Thrombin-invA aptamer

<400> SEQUENCE: 2
cactggtagg ttggtgtggt tggggccagt gggcatcaat actcatctgt ttaccggg   58

<210> SEQ ID NO 3
<211> LENGTH: 27
<212> TYPE: DNA
<213> ORGANISM: Artificial Sequence
<220> FEATURE:
<223> OTHER INFORMATION: experimental model for verifying assay system:
      Synthetic target DNA derived from Salmonella invA gene

<400> SEQUENCE: 3
cccggtaaac agatgagtat tgatgcc                                   27

<210> SEQ ID NO 4
<211> LENGTH: 27
<212> TYPE: DNA
<213> ORGANISM: Artificial Sequence
<220> FEATURE:
<223> OTHER INFORMATION: experimental model for verifying assay system:
      Synthetic control DNA used in detection of Salmonella invA gene

<400> SEQUENCE: 4
gaatccggta ctggctaaga caactgt                                   27

<210> SEQ ID NO 5
<211> LENGTH: 58
<212> TYPE: DNA
<213> ORGANISM: Artificial Sequence
<220> FEATURE:
<223> OTHER INFORMATION: experimental model for verifying assay system:
      Synthetic Thrombin-SARS aptamer

<400> SEQUENCE: 5
cactggtagg ttggtgtggt tggacgacga attcatgatc acgtccttgg ggccagtg   58

<210> SEQ ID NO 6
<211> LENGTH: 15
<212> TYPE: DNA
<213> ORGANISM: Artificial Sequence
<220> FEATURE:
<223> OTHER INFORMATION: experimental model for verifying assay system:
      Synthetic target DNA derived from SARS virus gene

<400> SEQUENCE: 6
tgatcatgaa ttcgt                                                15

<210> SEQ ID NO 7
<211> LENGTH: 15
<212> TYPE: DNA
<213> ORGANISM: Artificial Sequence
```

```
-continued

<220> FEATURE:
<223> OTHER INFORMATION: experimental model for verifying assay system:
      Synthetic control DNA used in the detection of SARS virus gene

<400> SEQUENCE: 7
attgctatcg tacat                                                          15

<210> SEQ ID NO 8
<211> LENGTH: 56
<212> TYPE: DNA
<213> ORGANISM: Artificial Sequence
<220> FEATURE:
<223> OTHER INFORMATION: experimental model for verifying assay system:
      Synthetic Thrombin-ATP aptamer

<400> SEQUENCE: 8
cactggtagg ttggtgtggt tctgggggag tattgcggag gaagttgggg ccagtg            56

<210> SEQ ID NO 9
<211> LENGTH: 67
<212> TYPE: DNA
<213> ORGANISM: Artificial Sequence
<220> FEATURE:
<223> OTHER INFORMATION: experimental model for verifying assay system:
      Synthetic Thrombin-invA- 3'5' aptamer

<400> SEQUENCE: 9
actcatctgt ttaccgggca ctggtaggtt ggtgtggttg gggccagtgc ttcaaatcgg        60
catcaat                                                                   67

<210> SEQ ID NO 10
<211> LENGTH: 36
<212> TYPE: DNA
<213> ORGANISM: Artificial Sequence
<220> FEATURE:
<223> OTHER INFORMATION: experimental model for verifying assay system:
      Synthetic target nucleotide sequence InvADNA

<400> SEQUENCE: 10
cccggtaaac agatgagtat tgatgccgat ttgaag                                   36

<210> SEQ ID NO 11
<211> LENGTH: 36
<212> TYPE: DNA
<213> ORGANISM: Artificial Sequence
<220> FEATURE:
<223> OTHER INFORMATION: experimental model for verifying assay system:
      Synthetic control DNA used to detect thrombin activity

<400> SEQUENCE: 11
attgtacttg gactgtgcat tagcatgtta cagtca                                   36
```